United States Patent
Mitelberg et al.

(10) Patent No.: US 7,371,251 B2
(45) Date of Patent: *May 13, 2008

(54) STRETCH RESISTANT EMBOLIC COIL DELIVERY SYSTEM WITH MECHANICAL RELEASE MECHANISM

(75) Inventors: Vladimir Mitelberg, Aventura, FL (US); Donald K. Jones, Lauderhill, FL (US); Juan A. Lorenzo, Davie, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 202 days.

This patent is subject to a terminal disclaimer.

(21) Appl. No.: 11/143,052

(22) Filed: Jun. 2, 2005

(65) Prior Publication Data

US 2006/0276824 A1    Dec. 7, 2006

(51) Int. Cl.
*A61M 29/00* (2006.01)
*A61F 2/06* (2006.01)
(52) U.S. Cl. ............ 606/200; 606/191; 623/1.11
(58) Field of Classification Search .......... 606/142, 606/151, 191, 200, 213; 623/1.1, 1.11
See application file for complete search history.

(56) References Cited

U.S. PATENT DOCUMENTS

| | | | |
|---|---|---|---|
| 5,108,407 A | 4/1992 | Geremia et al. | |
| 5,122,136 A | 6/1992 | Guglielmi et al. | |
| 5,250,071 A | 10/1993 | Palermo | |
| 5,263,964 A | 11/1993 | Purdy | |
| 5,334,210 A | 8/1994 | Gianturco | |
| 5,350,397 A | 9/1994 | Palermo et al. | |
| 5,382,259 A | 1/1995 | Phelps et al. | |
| 5,540,680 A | 7/1996 | Guglielmi et al. | |
| 5,582,619 A * | 12/1996 | Ken ..................... | 606/191 |
| 5,601,600 A | 2/1997 | Ton et al. | |
| 5,800,455 A | 9/1998 | Palermo et al. | |
| 5,853,418 A | 12/1998 | Ken et al. | |
| 5,895,391 A | 4/1999 | Farnholtz | |
| 5,895,411 A | 4/1999 | Irie | |
| 5,925,059 A * | 7/1999 | Palermo et al. ........ | 606/191 |
| 6,113,622 A | 9/2000 | Hieshima | |

(Continued)

OTHER PUBLICATIONS

European Search Report EP 06 25 2706 dated Sep. 11, 2006 with Annex to the European Search Report.

*Primary Examiner*—(Jackie) Tan-Uyen Ho
*Assistant Examiner*—Melissa Ryckman
(74) *Attorney, Agent, or Firm*—Michael W. Montgomery

(57) ABSTRACT

A medical device for placing an embolic device at a predetermined site within a vessel of the body including a delivery catheter and a flexible pusher member having a lumen therethrough and being slidably disposed within the lumen of the catheter. A stretch resistant embolic device is retained within the delivery catheter by a mechanical interlocking mechanism which includes an engagement member which is attached to the distal end of the pusher member and extends through a retaining ring at the proximal end of the embolic device. A detachment member extends through an aperture at the distal end of the engagement member thereby locking the embolic device onto the pusher member. The engagement member engages a retaining ring on the embolic device. When the embolic device is advanced to the predetermined site within the vessel, the detachment member is withdrawn from the aperture to thereby release the embolic device at the treatment site.

38 Claims, 7 Drawing Sheets

U.S. PATENT DOCUMENTS

| | | | |
|---|---|---|---|
| 6,193,728 B1 | 2/2001 | Ken et al. | |
| 6,203,547 B1 | 3/2001 | Nguyen et al. | |
| 6,238,415 B1 | 5/2001 | Sepetka et al. | |
| 6,500,149 B2 | 12/2002 | Gandhi et al. | |
| 6,537,314 B2 | 3/2003 | Langberg et al. | |
| 6,660,020 B2 | 12/2003 | Wallace et al. | |
| 6,793,673 B2 | 9/2004 | Kowalsky et al. | |
| 6,835,185 B2 | 12/2004 | Ramzipoor | |
| 6,849,303 B2 | 2/2005 | Dave | |
| 6,902,572 B2 * | 6/2005 | Beulke et al. | 606/200 |
| 2001/0002438 A1 | 5/2001 | Sepetka et al. | |
| 2002/0111647 A1 | 8/2002 | Khairkhahan et al. | |
| 2002/0165569 A1 | 11/2002 | Ramzipoor et al. | |
| 2004/0034363 A1 | 2/2004 | Wilson et al. | |
| 2004/0044361 A1 | 3/2004 | Frazier et al. | |
| 2004/0111095 A1 | 6/2004 | Gordon et al. | |
| 2005/0043755 A1 | 2/2005 | Wilson et al. | |
| 2005/0113864 A1 | 5/2005 | Gandhi et al. | |
| 2006/0276824 A1 * | 12/2006 | Mitelberg et al. | 606/200 |
| 2006/0276825 A1 * | 12/2006 | Mitelberg et al. | 606/200 |
| 2006/0276826 A1 * | 12/2006 | Mitelberg et al. | 606/200 |
| 2006/0276827 A1 * | 12/2006 | Mitelberg et al. | 606/200 |
| 2006/0276828 A1 * | 12/2006 | Balgobin et al. | 606/200 |
| 2006/0276829 A1 * | 12/2006 | Balgobin et al. | 606/200 |
| 2006/0276830 A1 * | 12/2006 | Balgobin et al. | 606/200 |
| 2006/0276832 A1 * | 12/2006 | Balgobin et al. | 606/200 |
| 2006/0276833 A1 * | 12/2006 | Balgobin et al. | 606/200 |
| 2006/0276834 A1 * | 12/2006 | Balgobin et al. | 606/200 |
| 2007/0010849 A1 * | 1/2007 | Balgobin et al. | 606/200 |
| 2007/0010850 A1 * | 1/2007 | Balgobin et al. | 606/200 |
| 2007/0118172 A1 * | 5/2007 | Balgobin et al. | 606/200 |

* cited by examiner

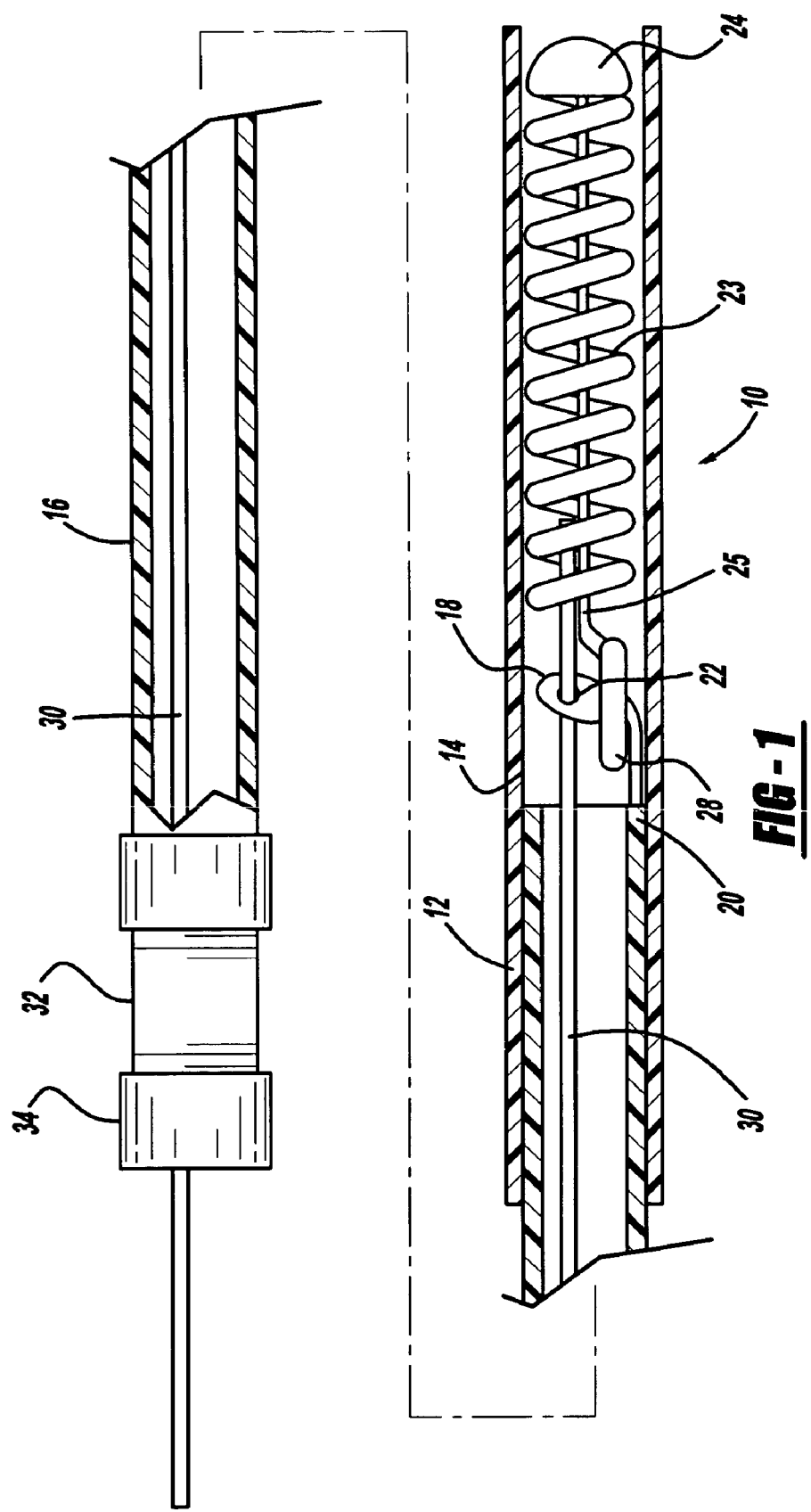

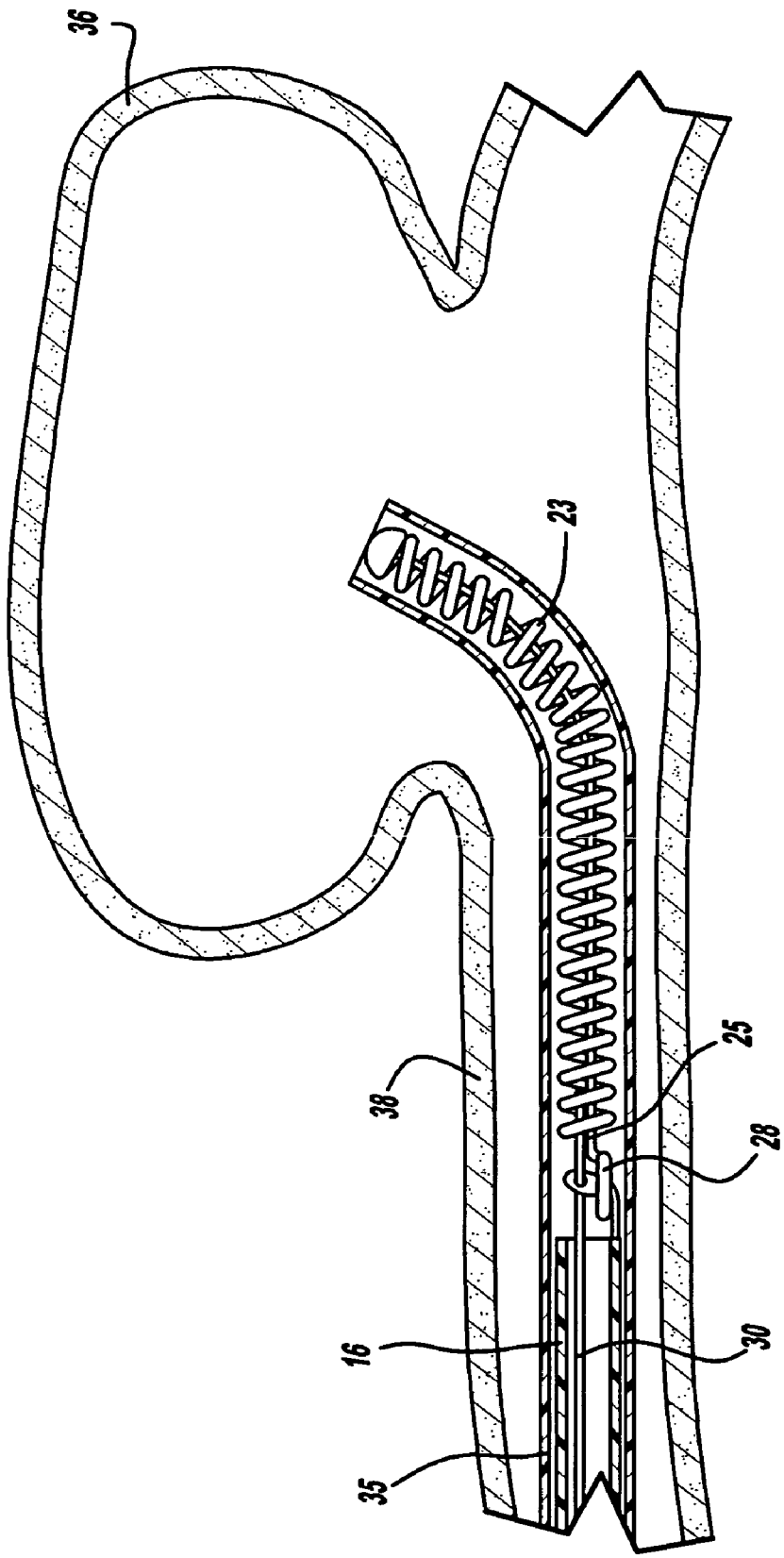

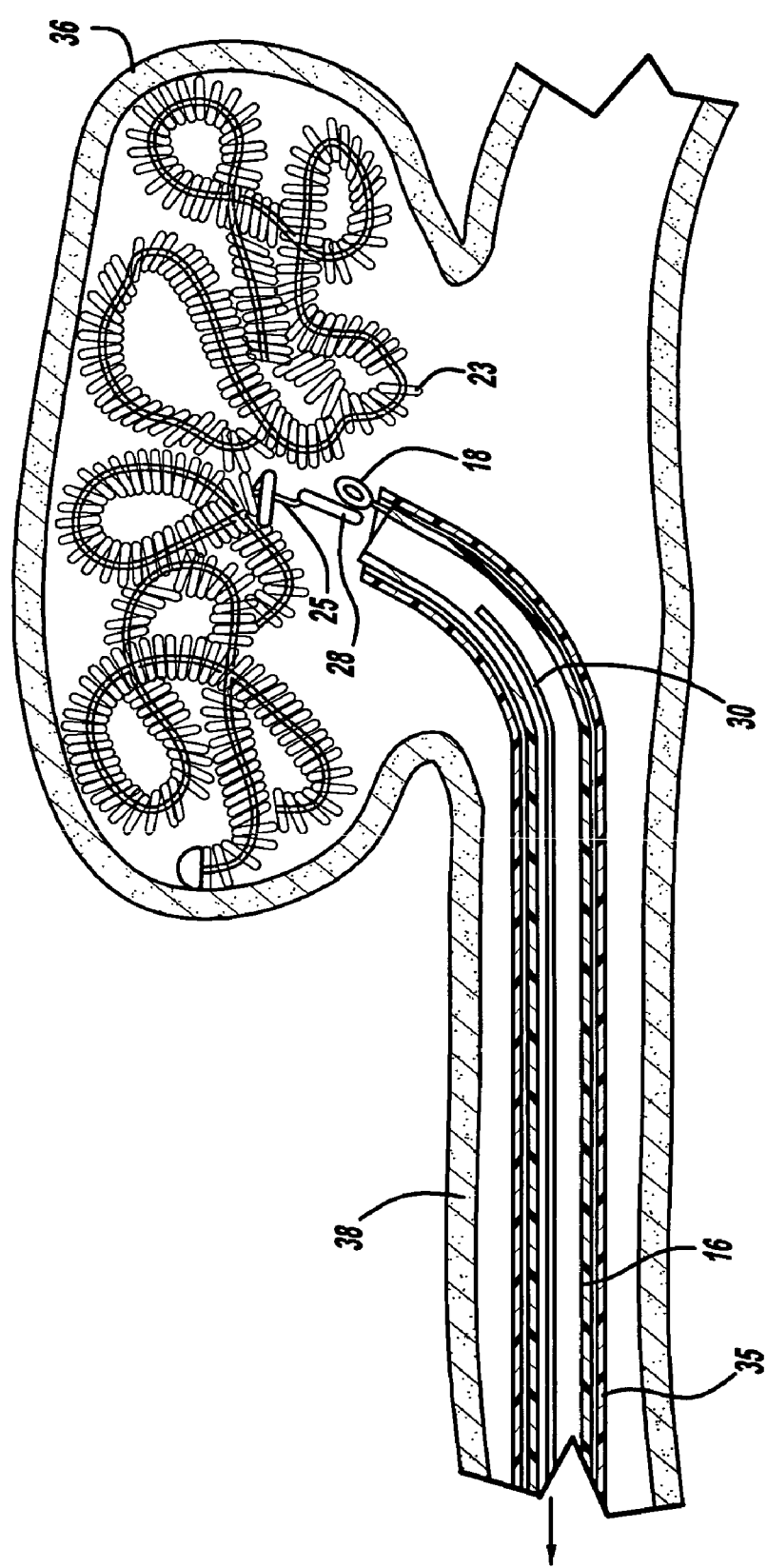

STRETCH RESISTANT EMBOLIC COIL DELIVERY SYSTEM WITH MECHANICAL RELEASE MECHANISM

BACKGROUND OF INVENTION

1. Field of the Invention

The present invention relates to a medical device for placing a stretch resistant embolic device at a predetermined site within a vessel of the human body, and more particularly, relates to a catheter-based deployment system for delivering an embolic device. This device is particularly suited to transport an embolic device, such as a stretch resistant embolic coil, through the tortious vasculature of the human brain to a selected site within the vessel or within an aneurysm.

2. Description of the Prior Art

For many years, flexible catheters have been used to place various devices within the vessels of the human body. Such devices include dilation balloons, radiopaque fluids, liquid medications, and various types of occlusion devices such as balloons and embolic coils. Examples of such catheter-based devices are disclosed in U.S. Pat. No. 5,108,407, entitled, "Method and Apparatus for Placement of an Embolic Coil" and U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas." These patents disclose catheter-based devices for delivering embolic coils to preselected positions within vessels of the human body in order to treat aneurysms, or alternatively, to occlude blood vessels at a particular location.

Coils which are placed in vessels may take the form of helically wound coils, or alternatively, may take the form of randomly wound coils, coils wound within coils or other such coil configurations. Examples of various coil configurations are disclosed in U.S. Pat. No. 5,334,210, entitled, "Vascular Occlusion Assembly" and U.S. Pat. No. 5,382,259 entitled, "Vasoocclusion Coil with Attached Tubular Woven or Braided Fibrous Covering." Embolic coils are generally formed of a radiopaque metallic material, such as platinum, gold, tungsten, or alloys of these metals. Often, several coils are placed at a given location to occlude the flow of blood through the vessel, or aneurysm, by promoting thrombus formation at the particular site.

In the past, embolic coils have been placed within the distal end of a catheter. When the distal end of the catheter is properly positioned, the coil may then be pushed out of the end of the catheter with a pusher member to release the coil at the desired location. This procedure for placement of an embolic coil is conducted under fluoroscopic visualization such that the movement of the coil through the vasculature of the body may be monitored and the coil placed at the desired location.

Another procedure involves the use of glue or solder for attaching the coil to a guidewire, which in turn, is placed within a flexible catheter for positioning the coil within the vessel at a preselected position. Once the coil is in the desired position, the coil is held in position by the catheter and the guidewire is pulled proximally to thereby cause the coil to become detached from the guidewire and released from the catheter. Such a coil positioning system is disclosed in U.S. Pat. No. 5,263,964 entitled, "Coaxial Traction Detachment Apparatus and Method."

Still another coil positioning procedure is that of having a catheter with a socket at the distal end of the catheter for retaining a ball which is, in turn, bonded to the proximal end of the coil. The ball, which is generally larger in diameter than the outside diameter of the coil, is placed in the socket within the lumen at the distal end of the catheter and the catheter is then moved into a vessel in order to place the coil at a desired position. Once the position is reached, a pusher wire with a piston at the end thereof is pushed distally from the proximal end of the catheter to push the ball out of the socket in order to release the coil at the desired position. Such a system is disclosed in U.S. Pat. No. 5,350,397, entitled, "Axially Detachable Embolic Coil Assembly."

Another procedure for placing an embolic coil within a vessel is that of using a heat releasable adhesive bond for retaining the coil at the distal end of the catheter. One such system uses laser energy transmitted through a fiber optic cable to apply heat to the adhesive bond in order to release the coil from the end of the catheter. Such a procedure is disclosed in U.S. Pat. No. 5,108,407, entitled "Method and Apparatus for Placement of an Embolic Coil."

Yet another coil deployment system incorporates a catheter having a lumen throughout the length of the catheter and a distal tip for retaining the coil for positioning the coil at a preselected site. The distal tip of the catheter is formed of a material which exhibits the characteristic that when the lumen of the catheter is pressurized the distal tip expands radially to release the coil at the preselected site. Such a deployment system is disclosed in U.S. Pat. No. 6,113,622, entitled, "Embolic Coil Hydraulic Deployment System."

Still another coil deployment system incorporates an interlocking mechanism on the coil. The interlocking end on the embolic coil couples with a similar interlocking mechanism on a pusher assembly. A control wire which extends through the locking mechanism secures the coil to the pusher assembly. The pusher assembly and embolic coil are initially disposed within the lumen of a catheter. When the embolic coil is pushed out of the end of the catheter for placement, the control wire is retracted and the coil disengages from the pusher assembly. Such a deployment system is disclosed in U.S. Pat. No. 5,925,059, entitled, "Detachable Embolic Coil Assembly."

Yet another coil deployment system incorporates an embolic device detachably mounted on the distal portion of a pusher member and held in place with a connector thread or fiber. The fiber passes through a cutter member that may be activated to cut the connector fiber. Once the connector fiber is cut, the embolic device is released. Such a deployment system is disclosed in Published U.S. Patent Application No. 2002/0165569, entitled, "Intravascular Device Deployment Mechanism Incorporating Mechanical Detachment."

Still another coil deployment system incorporates an embolic device with a stretch resistant member therethrough. The distal end of the stretch resistant member attaches to the embolic coil and the proximal end of the stretch resistant member is detachably mounted on the pusher member through various means such as adhesive, or by a connector fiber adhered to or tied to the pusher member, and is detachable by the application of heat. Such a deployment system is disclosed in Published U.S. Patent Application No. 2004/0034363, entitled, "Stretch Resistant Therapeutic Device."

Still another coil deployment system incorporates a pusher wire with a stiff wavy-shaped end segment which is coupled to the embolic coil and is placed in the lumen of the catheter. The coil is advanced through the catheter until it reaches a predetermined site in the vessel at which time the pusher wire is retracted and the embolic coil is released. Such a system is disclosed in U.S. Pat. No. 6,203,547, entitled, "Vaso-occlusion Apparatus Having A Manipulable Mechanical Detachment Joint And A Method For Using The Apparatus."

A still further embolic device deployment system for placement of an embolic device, or coil, includes a delivery catheter and a flexible pusher member. The embolic device is retained by an interlocking mechanism which includes a detachment member which extends through an aperture in an engagement member. The engagement member engages a ring on the embolic device. When the detachment member is withdrawn from the aperture, the embolic device is released. One such deployment system is disclosed in a concurrently filed patent application U.S. Ser. No. 11/143,051, entitled, "Embolic Coil Delivery System With Mechanical Release Mechanism," (Attorney Docket No. CRD5194USNP0), and assigned to the same assignee as the present application.

SUMMARY OF THE INVENTION

The present invention is directed toward a vascular occlusive embolic device deployment system for use in placing a stretch-resistant embolic device at a predetermined site within a vessel which includes an elongated flexible catheter, an elongated pusher member having a lumen extending therethrough and being slidably disposed within the lumen of the catheter. The embolic device takes the form of an embolic coil defining a central lumen extending between the proximal and distal ends of the coil. A stretch resistant member, such as a platinum wire, having first and second ends in which the first end of the stretch resistant member is attached to the distal section of the coil and the second end of the stretch resistant member is attached to a retaining ring. An engagement member, preferably having an L-shaped configuration, is fixedly attached to the distal end of the pusher member and includes an aperture extending through the distal end thereof. The engagement member extends through the retaining ring of the stretch-resistant embolic device. In addition, the deployment system includes an elongated detachment member which extends from the proximal end of the pusher member, through the lumen of the pusher member and through the aperture of the engagement member such that when the detachment member is pulled proximally the distal end of the detachment member is withdrawn from the aperture of the engagement member to thereby release the embolic device.

In accordance with another aspect of the present invention, there is provided a deployment system for use in placing an embolic device at a predetermined site within a vessel which includes an elongated flexible catheter, an elongated pusher member being slidably disposed within the lumen of the catheter. The embolic device takes the form of an embolic coil defining a central lumen extending between the proximal and distal ends of the coil. A stretch resistant member having first and second ends in which the first end of the stretch resistant member is attached to the distal section of the coil and the second end of the stretch resistant member is attached to a retaining ring. An engagement member, preferably having an L-shaped configuration, is fixedly attached to the distal end of the pusher member and includes an aperture extending through the distal end thereof. The engagement member extends through the retaining ring of the stretch-resistant embolic device. In addition, the deployment system includes an elongated detachment member which extends from the proximal end of the catheter through the lumen of the catheter and through the aperture of the engagement member such that when the detachment member is pulled proximally the distal end of the detachment member is withdrawn from the aperture of the engagement member to thereby release the embolic device.

In accordance with another aspect of the present invention, the second end of the stretch-resistant member is attached to the proximal section of the coil, as opposed to the retaining ring, to prevent the coil from stretching, and the proximal end of the coil is attached to the retaining ring.

In accordance with another aspect of the present invention, the engagement member is of an L-shaped configuration and one of the legs is attached to the pusher member and the other leg extends through the retaining ring. The aperture extends through the leg which extends through the retaining ring such that when the detachment member extends through the aperture the retaining ring of the embolic device is interlocked onto the engagement member until the detachment member is withdrawn from the aperture. In accordance with another aspect of the present invention, the aperture has a central axis which extends substantially at a right angle to the central axis of the retaining ring. In addition, the embolic device takes the form of a helically wound embolic coil having a central axis which extends at a right angle to the central axis of the retaining ring. The stretch resistant member is attached to and extends from a distal section to a proximal section of the helically wound coil.

In accordance with still anther aspect of the present invention, the embolic device takes the form of a helically wound coil formed of a plurality of turns of which one turn has a central axis which extends at a right angle to the central axis of the other turns to thereby form the retaining ring.

In addition, the vascular embolic device deployment system preferably includes a retaining clamp mounted on the proximal end of the pusher member, and the detachment member extends from a position proximal of the retaining clamp and through a lumen in the clamp in order that the detachment member may be clamped in a fixed position prior to the release of the embolic device. Upon release of the clamp, the detachment member may be withdrawn from the aperture of the engagement member to thereby release the embolic device.

BRIEF DESCRIPTION OF THE DRAWINGS

FIG. 1 is an enlarged, partially sectional view of an embodiment of an embolic device deployment system in accordance with the present invention;

FIGS. 3, 3A, 3B, and 3C are enlarged, sectional views of the coil deployment system shown in FIGS. 1 and 2 illustrating the sequential steps in the advancement of the embolic device, removal of a detachment member, and release of the embolic device.

DESCRIPTION OF THE PREFERRED EMBODIMENT

Figure 1A:
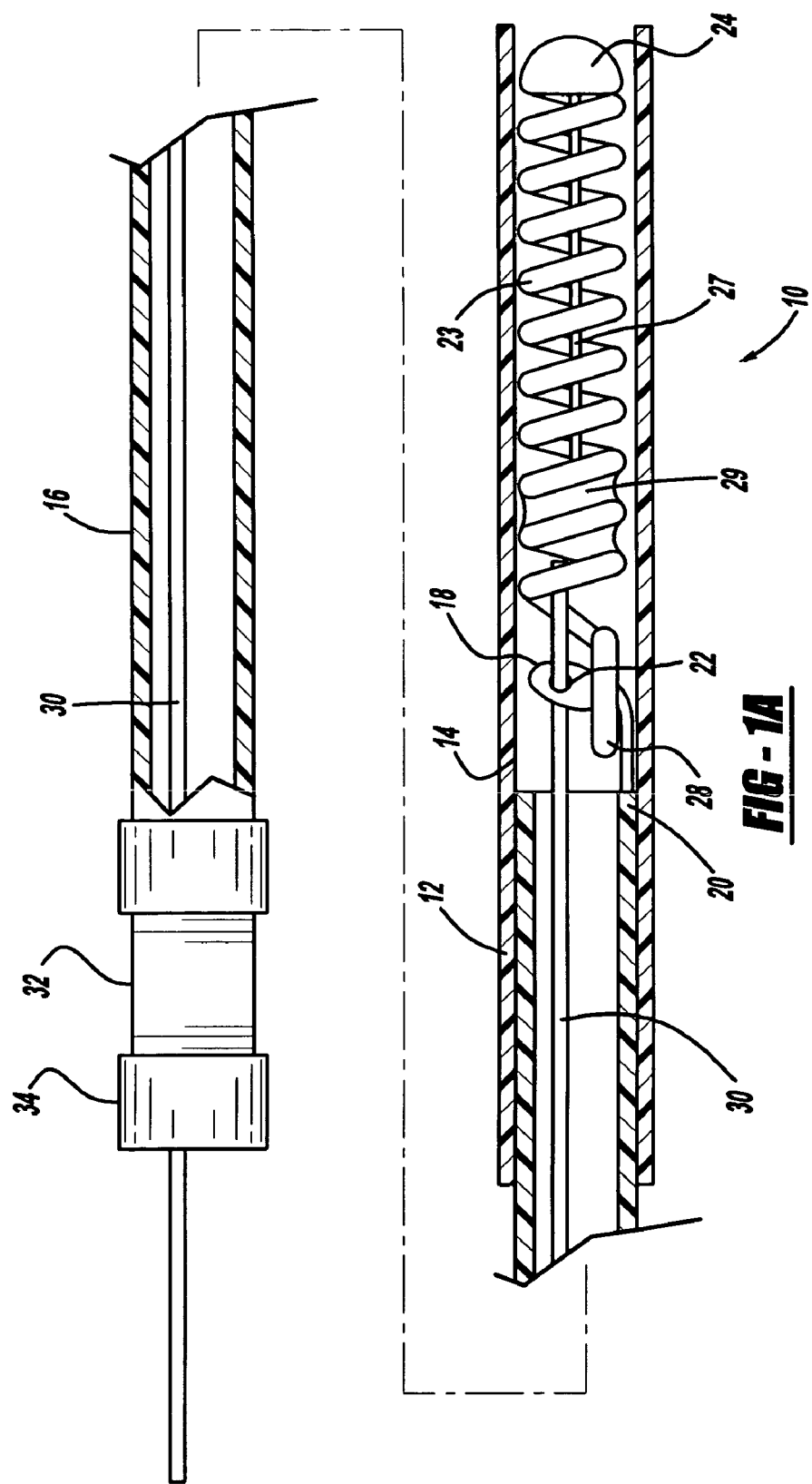
FIG. 1A is an enlarged, partially sectional view of a second embodiment of an embolic device deployment system in accordance with the present invention.

FIG. 1 generally illustrates one embodiment of a vascular occlusive embolic device deployment system 10 which includes a sheath introducer 12 having a lumen 14 extending therethrough and having an elongated pusher member 16 slidably disposed within the lumen 14 of the sheath introducer 12. An elongated engagement member 18 is slidably disposed within a lumen of the pusher member 16 and has an aperture 22 extending through the distal end thereof. The central axis of the aperture 22 extends generally parallel to the axis of the pusher member 16. The engagement member 18 is preferably formed of a small diameter resilient wire, such as Nitinol, and includes a flattened distal end having a passageway extending therethrough to form the aperture 22.

The deployment system 10 also includes an embolic device 23, which as illustrated, preferably takes the form of a helically wound embolic coil, which is disposed in the distal section of the sheath introducer 12. While the embolic device as illustrated is shown as a helically wound coil various other types of embolic devices, such as filaments, braids, foams, expandable meshes and stents, could be delivered using the present deployment system and various other coil configurations could be delivered using this system. A weld, or solder, bead 24 is formed at the distal end of the embolic device 23 to provide an atraumatic tip for the embolic device. In addition, the distal end of a stretch-resistant member 25, which preferably takes the form of a platinum wire, is attached to the distal bead 24 and extends proximally through the central lumen of the coil. While the stretch-resistant member preferably takes the form of a platinum wire, other materials or composites such as polymers, metals and ceramics, having a low elongation relative to the coil elongation may also be suitable. Alternatively, the distal end of the stretch-resistant member could be attached to the coil at a more proximal location in the distal section of the coil. The proximal end of the stretch resistant member is then attached to the edge of the retaining ring 28. Preferably, the retaining ring 28 has a central axis which extends at right angles to the central axis of the sheath introducer 12 and also extends at right angles to the central axis of the helically wound embolic coil.

FIG. 1A illustrates another variation of the stretch-resistant embolic device 23 in which the distal end of a stretch-resistant member 27 is attached to the bead 24 at the distal end of the coil and the proximal end of the stretch-resistant coil is attached to the turns in the proximal section of the coil by use of a weld, or solder, bead 29. With this embodiment, the most proximal end of the coil is attached to the retaining ring 28.

As illustrated in FIGS. 1, 1A, 2A and 2B, the engagement member 18 extends in a direction parallel to the central axis of the pusher member 16 and extends through the retaining ring 28 and is constrained in a generally L-shaped configuration by a detachment member 30. The elongated detachment member 30 extends from the proximal end of the deployment system 10 and through a lumen in the pusher member and then through the aperture 22 of the engagement member 18 and serves the function of interlocking the embolic device 23 to the pusher member 16 until such time as the detachment member 30 is withdrawn proximally. When the detachment member 30 is withdrawn from the aperture 22, the engagement member 18 returns to its normal straight configuration thereby releasing the retaining ring 28. The detachment member 30 preferably takes the form of a small diameter elongate filament, however, other forms such as wires or tubular structures are also suitable. While the detachment member 30 is preferably formed of nitinol, other metals and materials such as, stainless steel, PTFE, nylon, ceramic or glass fiber and composites may also be suitable.

Figure 2A:
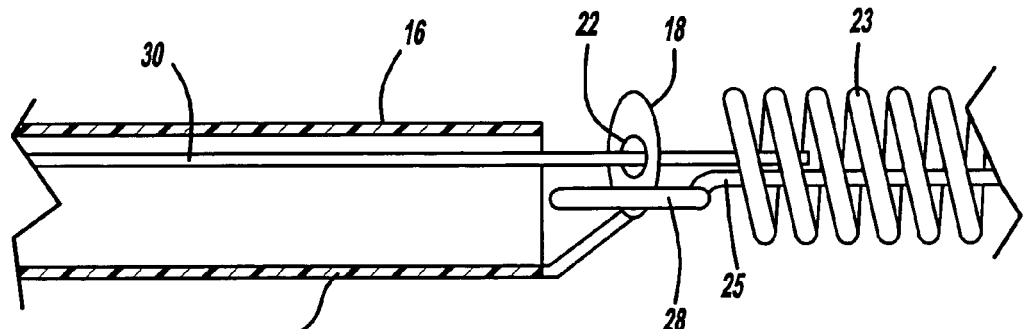
FIGS. 2A, 2B and 2C are enlarged, sectional views, illustrating in more detail the coil deployment system of FIG. 1.
Figure 2B:
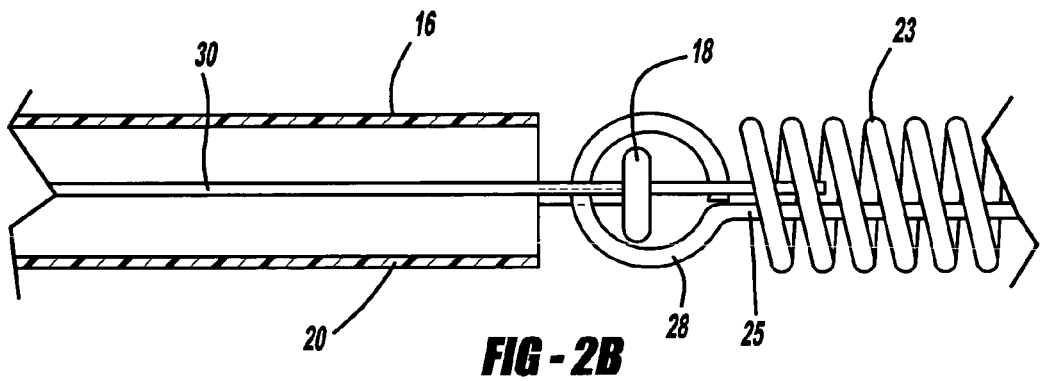
Figure 2C:
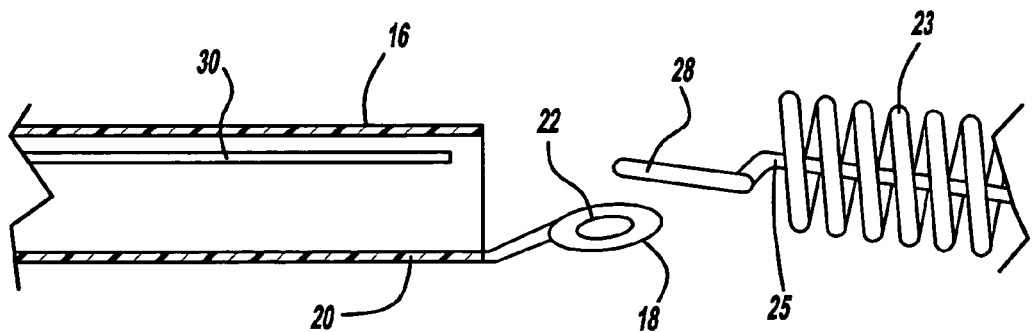

A Tuohy-Borst type of clamp 32 is mounted on the proximal end of the pusher member 16 and when tightened onto the detachment member 30 and onto the engagement member 18 and serves to prevent movement of the detachment member and the engagement member 18 until such time as the clamping cap 34 is loosened to release the grip onto these members. FIGS. 2A and 2B illustrate the interlocking arrangement between the embolic device 23 and the pusher member 16 as shown in FIG. 1, however, these latter figures illustrate the operation of the deployment system once the pusher member 16 has been moved distally to a position so that the distal end of the pusher member 16 extends slightly out of the distal end of the sheath introducer 12 or a delivery catheter thereby exposing the embolic device 23. As illustrated in FIG. 2C, once the embolic device 23 has been moved out of the end of the sheath introducer 12 the detachment member 30 may be pulled proximally to withdraw the detachment member from the aperture 22 of the engagement member 18 to thereby cause the engagement member to disengage from the retaining ring 28 of the embolic device thereby releasing the embolic device 23 at a preselected position. Alternatively, if desired, the detachment sequence described above and illustrated in FIGS. 2A, 2B and 2C may be executed while the embolic device 23 is still within the lumen of sheath introducer 12 or a delivery catheter.

One of the important advantages of the present invention is that the embolic device may be placed at a desired location within a vessel, or within an aneurysm, with the configuration of the device deployment system as shown in FIGS. 2A and 2B. If it is determined that the embolic device is improperly positioned, the embolic device 23 may then be withdrawn from that location and placed at another location, or even removed from the body by first withdrawing the pusher member 16 and the embolic device totally back into the delivery catheter. Once the embolic device has been entirely withdrawn back into the delivery catheter, the catheter may then be moved to a more desirable location and the embolic device may then be released at the new location. With the addition of the stretch resistant member 25, the embolic device may be withdrawn without concern that the coil will stretch and become very difficult to remove.

Figure 3A:
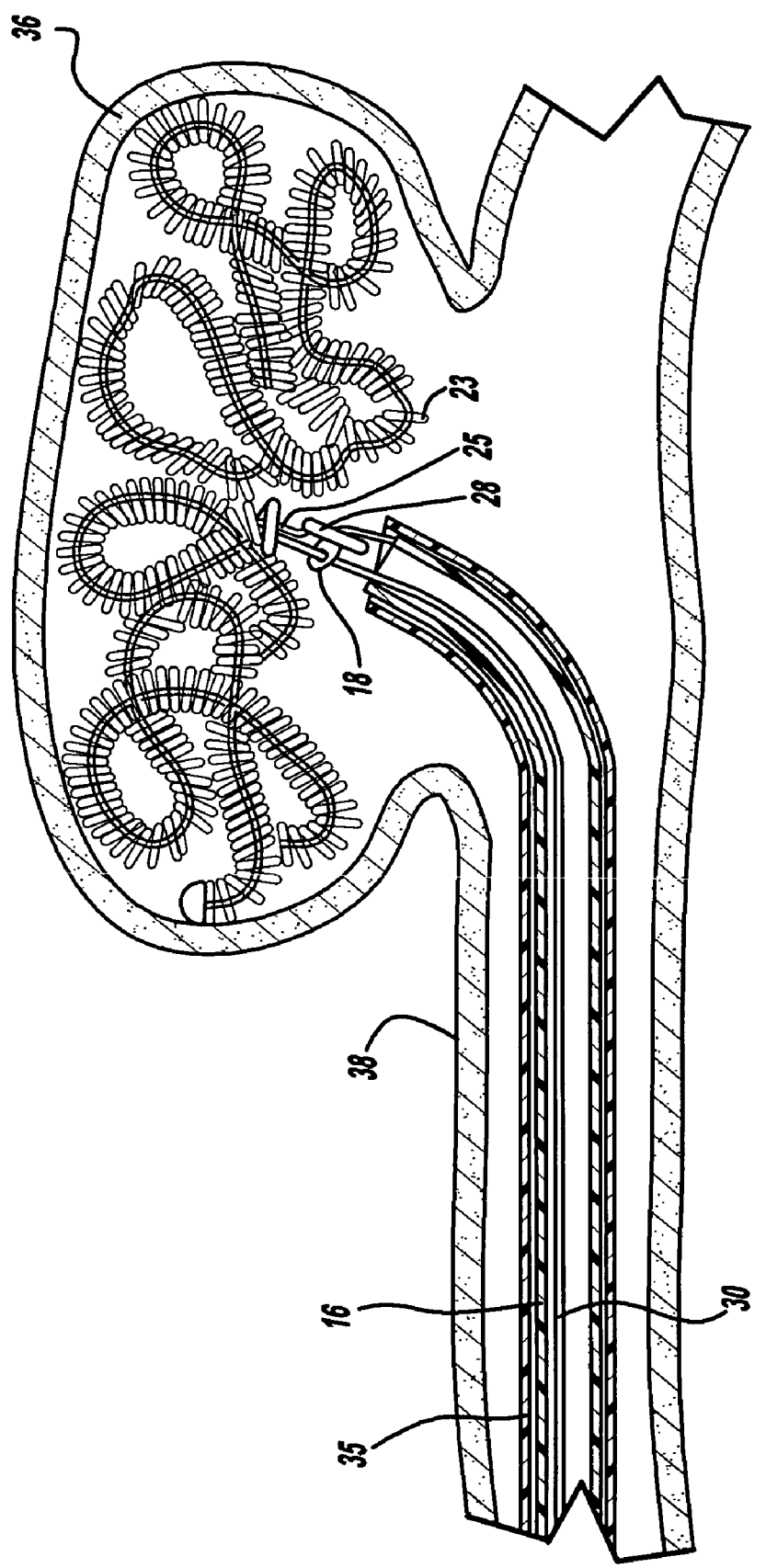

FIGS. 3, 3A and 3B generally illustrate the sequence of placing an embolic device, such as a helical wound coil into an aneurysm 36 which extends from a vessel wall 38. More particularly, FIG. 3 illustrates the vascular occlusive embolic device deployment system 10 in the same configuration as shown in FIG. 1 after the pusher member and associated embolic device have been inserted into a delivery catheter 35 and advanced into a position for deployment of the embolic device 23, shown as a helical embolic coil, into the aneurysm 36. FIG. 3A illustrates the deployment device having a configuration similar to FIG. 2A with the embolic device 23 being placed within the aneurysm 36 but prior to withdrawal of the detachment member 30. At this point, prior to the withdrawal of the detachment member 30, as previously mentioned, if it is determined that the embolic device has been improperly placed, the pusher member may be withdrawn thereby withdrawing the embolic device back into the delivery catheter 35 for repositioning to a different location, or alternatively, to remove the embolic coil entirely from the body.

Figure 3C:
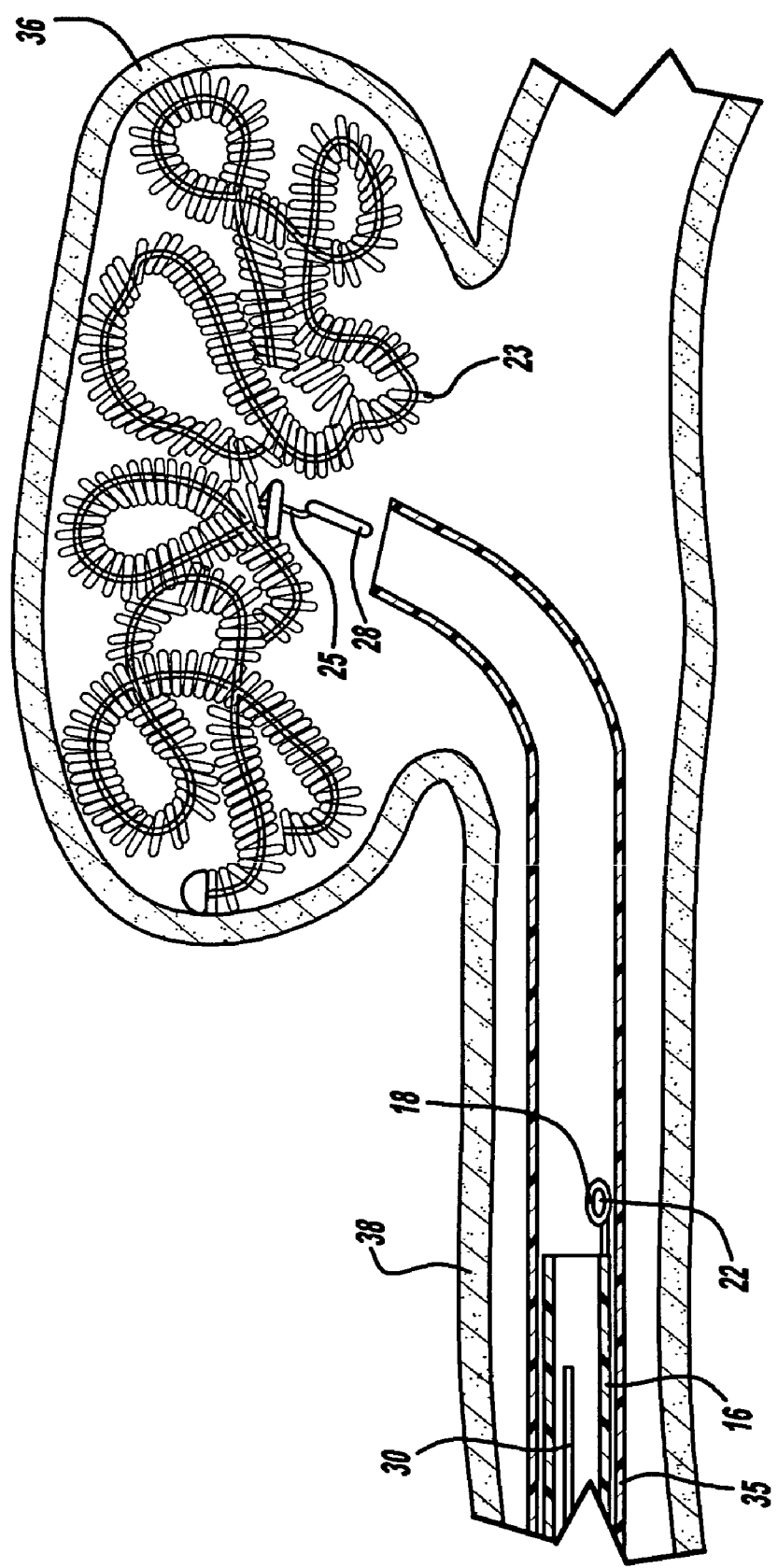

FIG. 3B illustrates the deployment device after the detachment member 30 has been removed from the engagement member 18 thereby releasing the embolic device within the aneurysm 36, and FIG. 3C illustrates the deployment device after the pusher member 16 has been withdrawn back into the delivery catheter 35 at the completion of the procedure or alternatively in order to insert a second coil through the delivery catheter 35 and into the same aneurysm.

As is apparent, there are numerous modifications of the preferred embodiment described above which will be readily apparent to one skilled in the art, such as many variations and modifications of the embolic device including numerous coil winding configurations, or alternatively other types of embolic devices. Also, there are many possible variations in the materials and configurations of the release mechanism. These modifications would be apparent to those having ordinary skill in the art to which this invention relates and are intended to be within the scope of the claims which follow.

That which is claimed is:

1. A vasooclusive embolic device deployment system for use in placing an embolic device at a predetermined site within a vessel comprising:
   an elongated flexible deployment catheter having a lumen extending therethrough and having proximal and distal ends;
   an elongated pusher member having a lumen extending therethrough and having proximal and distal ends and being slidably disposed within the lumen of the deployment catheter;
   an embolic device which takes the form of an embolic coil defining a central lumen extending between proximal and distal sections of the coil, a stretch resistant member having first and second ends, said first end of the stretch resistant member is attached to the distal section of the coil and the second end of the stretch resistant member is attached to a retaining ring;
   an engagement member fixedly attached to the distal end of the pusher member and having an aperture extending through the distal end thereof, said engagement member extending through said retaining ring; and,
   an elongated detachment member extending from a position proximal of the proximal end of the pusher member, through the lumen of the pusher member and through the aperture of the engagement member such that when the detachment member is pulled proximally the distal end of the detachment member is withdrawn from the aperture of the engagement member to thereby release the embolic device.

2. A vasooclusive embolic device deployment system as defined in claim 1, wherein said stretch resistant member is formed of a wire.

3. A vasooclusive embolic device deployment system as defined in claim 1, wherein said stretch resistant member is formed of a fiber.

4. A vasooclusive embolic device deployment system as defined in claim 1, wherein said stretch resistant member is formed of a polymer.

5. A vasooclusive embolic device deployment system as defined in claim 1, wherein said engagement member is of an L-shaped configuration so as to form first and second legs, said first leg being attached to said pusher member and said second leg extending through said retaining ring.

6. A vasooclusive embolic device deployment system as defined in claim 5, wherein said aperture extends through a distal end of said second leg such that when said detachment member extends through said aperture said retaining ring of said embolic device is interlocked onto said engagement member until the detachment member is withdrawn from said aperture.

7. A vasooclusive embolic device deployment system as defined in claim 6, wherein said stretch resistant member is formed of a wire.

8. A vasooclusive embolic device deployment system as defined in claim 6, wherein said stretch resistant member is formed of a fiber.

9. A vasooclusive embolic device deployment system as defined in claim 1, wherein the first end of said stretch-resistant member is attached to the distal end of the embolic coil.

10. A vasooclusive embolic device deployment system for use in placing an embolic device at a predetermined site within a vessel comprising:
    an elongated flexible deployment catheter having a lumen extending therethrough and having proximal and distal ends;
    an elongated pusher member having proximal and distal ends and being slidably disposed within the lumen of the deployment catheter;
    an embolic device which takes the form of an embolic coil defining a central lumen extending between proximal and distal sections of the coil, a stretch resistant member having first and second ends, said first end of the stretch resistant member is attached to the distal section of the coil and the second end of the stretch resistant member is attached to a retaining ring;
    an engagement member fixedly attached to the distal end of the pusher member and having an aperture extending through the distal end thereof; said engagement member extending through said retaining ring of the embolic device; and,
    an elongated detachment member extending from a position proximal of the deployment catheter, through the lumen of the catheter and through the aperture of the engagement member such that when the detachment member is pulled proximally the distal end of the detachment member is withdrawn from the aperture of the engagement member to thereby release the embolic device.

11. A vasooclusive embolic device deployment system as defined in claim 10, wherein said engagement member is of an L-shaped configuration so as to form first and second legs, said first leg being attached to said pusher member and said second leg extending through said retaining ring.

12. A vasooclusive embolic device deployment system as defined in claim 11, wherein said aperture extends through the distal end of said second leg such that when said detachment member extends through said aperture said retaining ring of said embolic device is interlocked onto said engagement member until the detachment member is withdrawn from said aperture.

13. A vasooclusive embolic device deployment system as defined in claim 12, wherein a central axis of said aperture extends substantially at a right angle to a central axis of said retaining ring.

14. A vasooclusive embolic device deployment system as defined in claim 13, wherein said embolic device takes the form of an embolic coil comprised of multiple turns.

15. A vasooclusive embolic device deployment system as defined in claim 14, wherein said embolic device takes the form of a helically wound embolic coil.

16. A vasooclusive embolic device deployment system as defined in claim 15, wherein said central axis of said retaining ring extends substantially at a right angle to a central axis of said helically wound embolic coil.

17. A vasooclusive embolic device deployment system as defined in claim 16, wherein said helically wound embolic coil is comprised of a plurality of turns of which one of said plurality of turns has a central axis which extends substantially at a right angle to a central axis of the other turns and forms the retaining ring.

18. A vasooclusive embolic device deployment system as defined in claim 10, including a retaining clamp having a lumen extending therethrough and being mounted on the proximal end of the pusher member, and wherein said detachment member extends from a position proximal of said clamp and through the lumen of the clamp so that said detachment member may be clamped into a fixed position prior to the release of the clamp and withdrawal of the detachment member from the aperture of the engagement member.

19. A vasooclusive embolic device deployment system for use in placing an embolic device at a predetermined site within a vessel comprising:
   an elongated flexible deployment catheter having a lumen extending therethrough and having proximal and distal ends;
   an elongated pusher member having a lumen extending therethrough and having proximal and distal ends and being slidably disposed within the lumen of the deployment catheter;
   an embolic device which takes the form of an embolic coil, a stretch resistant member having first and second ends, said first end of the stretch resistant member is attached to the distal section of the coil and the second end of the stretch-resistant member is attached to the proximal section of the coil, and the proximal end of said embolic coil is attached to a retaining ring;
   an engagement member fixedly attached to the distal end of the pusher member and having an aperture extending through the distal end thereof, said engagement member extending through said retaining ring; and,
   an elongated detachment member extending from a position proximal of the proximal end of the pusher member, through the lumen of the pusher member and through the aperture of the engagement member such that when the detachment member is pulled proximally the distal end of the detachment member is withdrawn from the aperture of the engagement member to thereby release the embolic device.

20. A vasooclusive embolic device deployment system as defined in claim 19, wherein said embolic device takes the form of an embolic coil.

21. A vasooclusive embolic device deployment system as defined in claim 20, wherein said embolic device takes the form of a helically wound embolic coil.

22. A vasooclusive embolic device deployment system as defined in claim 19, wherein said stretch resistant member is formed of a wire.

23. A vasooclusive embolic device deployment system as defined in claim 19, wherein said stretch resistant member is formed of a fiber.

24. A vasooclusive embolic device deployment system as defined in claim 19, wherein said stretch resistant member is formed of a polymer.

25. A vasooclusive embolic device deployment system as defined in claim 19, wherein said engagement member is of an L-shaped configuration so as to form first and second legs, said first leg being attached to said pusher member and said second leg extending through said retaining ring.

26. A vasooclusive embolic device deployment system as defined in claim 25, wherein said aperture extends through the distal end of said second leg such that when said detachment member extends through said aperture said retaining ring of said embolic device is interlocked onto said engagement member until the detachment member is withdrawn from said aperture.

27. A vasooclusive embolic device deployment system as defined in claim 26, wherein said stretch resistant member is formed of a wire.

28. A vasooclusive embolic device deployment system as defined in claim 26, wherein said stretch resistant member is formed of a fiber.

29. A vasooclusive embolic device deployment system as defined in claim 19, wherein the first end of said stretch-resistant member is attached to the distal end of the embolic coil.

30. A vasooclusive embolic device deployment system for use in placing an embolic device at a predetermined site within a vessel comprising:
   an elongated flexible deployment catheter having a lumen extending therethrough and having proximal and distal ends;
   an elongated pusher member having proximal and distal ends and being slidably disposed within the lumen of the deployment catheter;
   an embolic device which takes the form of an embolic coil defining a central lumen extending between the proximal and distal sections of the coil, a stretch resistant member having first and second ends, said first end of the stretch resistant member is attached to the distal section of the coil and the second end of the stretch resistant member is attached to a retaining ring;
   an engagement member fixedly attached to the distal end of the pusher member and having an aperture extending through the distal end thereof; said engagement member extending through said retaining ring of the embolic device; and,
   an elongated detachment member extending from a position proximal of the deployment catheter, through the lumen of the catheter and through the aperture of the engagement member such that when the detachment member is pulled proximally the distal end of the detachment member is withdrawn from the aperture of the engagement member to thereby release the embolic device.

31. A vasooclusive embolic device deployment system as defined in claim 30, wherein said engagement member is of an L-shaped configuration so as to form first and second legs, said first leg being attached to said pusher member and said second leg extending through said retaining ring.

32. A vasooclusive embolic device deployment system as defined in claim 31, wherein said aperture extends through the distal end of said second leg such that when said detachment member extends through said aperture said retaining ring of said embolic device is interlocked onto said engagement member until the detachment member is withdrawn from said aperture.

33. A vasooclusive embolic device deployment system as defined in claim 32, wherein a central axis of said aperture extends substantially at a right angle to a central axis of said retaining ring.

34. A vasooclusive embolic device deployment system as defined in claim 33, wherein said embolic device takes the form of an embolic coil.

35. A vasooclusive embolic device deployment system as defined in claim 34, wherein said embolic device takes the form of a helically wound embolic coil.

36. A vasooclusive embolic device deployment system as defined in claim 35, wherein said central axis of said retaining ring extends substantially at a right angle to a central axis of said helically wound embolic coil.

37. A vasooclusive embolic device deployment system as defined in claim 36, wherein said helically wound embolic coil is comprised of a plurality of turns of which one of said plurality of turns has a central axis which extends substantially at a right angle to a central axis of the other turns and forms the retaining ring.

38. A vasooclusive embolic device deployment system as defined in claim 30, including a retaining clamp having a lumen extending therethrough and being mounted on the proximal end of the pusher member, and wherein said detachment member extends from a position proximal of said clamp and through the lumen of the clamp so that said detachment member may be clamped into a fixed position prior to the release of the clamp and withdrawal of the detachment member from the aperture of the engagement member.

\* \* \* \* \*